(12) United States Patent
Bernard et al.

(10) Patent No.: US 6,946,538 B2
(45) Date of Patent: Sep. 20, 2005

(54) CATALYST FOR ISOCYANATE CONDENSATION, COMPOSITION CONTAINING SAME, METHOD FOR USE, AND RESULTING COMPOSITIONS

(75) Inventors: Jean-Marie Bernard, Mornant (FR); Damien Bonneau, Saint Clement (FR); Marc Visseau, Talant (FR)

(73) Assignee: Rhodia Chimie, Boulogne-Billancourt Cedex (FR)

( * ) Notice: Subject to any disclaimer, the term of this patent is extended or adjusted under 35 U.S.C. 154(b) by 0 days.

(21) Appl. No.: 10/450,261

(22) PCT Filed: Dec. 28, 2001

(86) PCT No.: PCT/FR01/04228
§ 371 (c)(1),
(2), (4) Date: Jun. 12, 2003

(87) PCT Pub. No.: WO02/053614
PCT Pub. Date: Jul. 11, 2002

(65) Prior Publication Data
US 2004/0024212 A1 Feb. 5, 2004

(30) Foreign Application Priority Data

Dec. 29, 2000 (FR) .............................. 00 17317
Dec. 29, 2000 (FR) .............................. 00 17323
Dec. 29, 2000 (FR) .............................. 00 17315
Dec. 21, 2001 (FR) .............................. 01 16723

(51) Int. Cl.$^7$ ............................................. C08G 18/79
(52) U.S. Cl. ................... 528/73; 252/182.2; 528/45; 544/222
(58) Field of Search .................. 252/182.2; 528/45, 528/73; 544/222

(56) References Cited

U.S. PATENT DOCUMENTS 4,003,859 A  1/1977  Reymore et al.
4,675,401 A  6/1987  Robin
4,801,663 A  * 1/1989  Ueyanagi et al. ........... 525/528
5,017,695 A  5/1991  Gradeff et al.

* cited by examiner

Primary Examiner—Rachel Gorr
(74) Attorney, Agent, or Firm—Burns, Doane, Swecker & Mathis, LLP

(57) ABSTRACT

The invention concerns a method for catalytic (cyclo) condensation of monomer isocyanates, characterised in that it comprises: a) reacting starting monomer isocyanates with a catalyst comprising a mineral or organic salt of a compound of formula (I), wherein $Y^-$ is selected among: a negatively charged oxygen atom, and a carbonaceous radical comprising a negative charge borne by an atom of column VB of the periodic table or by an oxygen atom advantageously by a nitrogen atom and whereof the bond with the silicon of formula (I) is borne by an atom of column VB of the periodic table, advantageously by a nitrogen atom; wherein $R_1$, $R_2$ and $R_3$, identical or different, represent a monovalent hydrocarbon radical having advantageously 1 to 30 carbon atoms, or a precursor of said compound, at a temperature of at least 20° C. and advantageously of at least 40° C. and not more than 200° C., advantageously not more than 150° C.; b) stopping the (cyclo)condensation reaction at the desired transformation rate; and c) optionally eliminating unreacted monomers or the reaction with other reactive compounds with the isocyanate function.

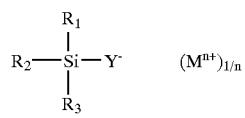

(I)

40 Claims, No Drawings

CATALYST FOR ISOCYANATE CONDENSATION, COMPOSITION CONTAINING SAME, METHOD FOR USE, AND RESULTING COMPOSITIONS

The invention relates to a novel process for the catalytic (cyclo)condensation, in particular (cyclo)trimerization, of isocyanates.

The trimerization, in particular cyclotrimerization, reaction of isocyanates is a known reaction generally catalyzed by:
- basic catalysts: quaternary ammoniums or their hydroxyalkyl derivatives, alkoxides, phenoxides, Mannich bases, tertiary amines, imide salts, and the like,
- organometallic catalysts: alkyl titanates, lead carboxylates, and the like.

However, the kinetics of this reaction depend on the structure of the isocyanate and it may be opportune to choose the catalyst according to the nature of the isocyanate.

Generally, quaternary ammonium carboxylates with the hydroxyalkyl functional group are the catalysts of choice for aliphatic diisocyanates. They give good results at low temperature (70 to 80° C.) and in low amount (of the order of 0.07% by weight with respect to the diisocyanate).

European patent EP 57 653 (Rhône-Poulenc) discloses hexamethyldisilazane (HMDZ) as trimerization catalyst for aliphatic diisocyanates. However, the amounts of catalyst used and the reaction temperatures are markedly greater than those employed for quaternary ammonium carboxylates, for example of the order of 1.25% by weight of catalyst with respect to HDI and 120° C.

The studies of the inventors which have led to the present invention have made it possible to discover that the polycondensation, in particular trimerization, reaction of isocyanate monomers could be carried out with salts with silazane or silanolate structures (nontoxic compounds) employed in a low amount at a not very high temperature with an excellent productive output, this being the case without resulting in significant coloring of the reaction medium.

Surprisingly, the kinetics of the trimerization reaction and the reactivity of the isocyanate monomers are substantially improved when a silazane salt is used in comparison with the corresponding protonated silazane derivative.

In addition, it has been surprisingly discovered that silazane salts or silanolates made it possible to catalyze the polycondensation, in particular the (cyclo)trimerization, of isocyanates in which the isocyanate functional group is hindered and therefore not very accessible, in particular the isocyanates in which the isocyanate functional group is carried by a secondary, in particular cycloaliphatic, tertiary or neopentyl carbon atom. What is more, the associated cations can be varied in order to balance, in an unusual way, the various oligocondensate entities resulting from the (cyclo)condensation.

Thus, according to the invention, saline compounds are used as catalysts for the (cyclo)condensation of an isocyanate functional group, advantageously an aliphatic, including cycloaliphatic, functional group, in which (cyclo)condensation said saline compound is selected from those which correspond to the formula:

where $(M^{n+})_{1/n}$ symbolizes the cocation(s) necessary for the electrical neutrality of said saline compound balancing the anion of formula (I):

where $Y^-$ is selected from:
- a negatively charged oxygen;
- and a carbonaceous radical comprising a negative charge carried by an atom from Group VB or by an oxygen, advantageously by a nitrogen, and for which the bond with the silicon of the above formula (I) is carried by an atom from Group VB, advantageously by a nitrogen;

where $R_1$, $R_2$ and $R_3$, which are identical or different, represent a monovalent hydrocarbonaceous group advantageously having from 1 to 30 carbon atoms which is optionally substituted by one or more halogen atoms or CN or ester groups and/or is optionally interrupted by one or more atoms selected from O, N and Si, advantageously of aliphatic nature, including of saturated or unsaturated cycloaliphatic and of aralkyl nature, or of aromatic nature, such as of aryl or alkylaryl nature;

and from those carrying a trialkylsilyl group and resulting from the reaction of said compounds of formula (I) and of an isocyanate functional group, advantageously an aliphatic isocyanate functional group.

This is because the anionic compounds of formula (I) are capable of forming compounds with the isocyanates, in particular resulting from the addition to the isocyanate functional group. The additions of the anion take place on the carbon of the isocyanate functional group.

Advantageously, Y represents a radical of formula (II):

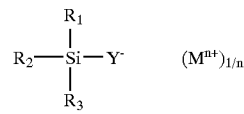

in which:
Z represents a semimetal from Group VB;
$R_{10}$ is selected from radicals comprising from 1 to 30 carbon atoms, including silyl and in particular trialkylsilyl; and
$R_{11}$ is selected from a negative (anionic) charge and a carbonaceous group (advantageously of at most 30 carbon atoms) attached to Z via a carbon simultaneously of $sp^2$ hybridization and carrying a nitrogen, the nitrogen of which carries a negative (anionic) charge.

According to one embodiment of the invention, it is possible, but without this exhibiting a specific advantage, for the anionic compound of formula 1 to exhibit more than one catalytically active sequence; according to this possibility, in this case, at least one of the $R_1$, $R_2$ and $R_3$ groups is interrupted by several atoms selected from O, N and Si, forming the sequence (I'):

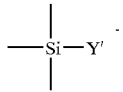

in which Y'⁻ represents a negatively charged oxygen atom or a sequence (II'):

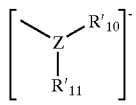

in which

Z' has the same values as Z;

$R'_{10}$ represents a hydrocarbonaceous group connected to the Z' radical via a carbon or a silicon (cf. $R_{10}$ radical);

$R'_{11}$ being the negative charge of Y' or a sequence on a nitrogen atom of Y' comprising an sp² carbon simultaneously bonded to Z' and carrying a nitrogen carrying the negative charge.

According to a preferred form of the present invention, the anionic compound of formula (I) where $R_{11}$ is a negative charge, $R_{10}$ advantageously exhibits at most 30 carbon atoms and is selected from hydrocarbonaceous radicals, in particular aryls, alkyls and silyls, and from carbonaceous groups attached to Z via a carbon which simultaneously is of sp² hybridization and carries a nitrogen.

In the latter case, it is preferable, when $R_{11}$ is a negative charge, for $R_{10}$ to advantageously exhibit at most 30 carbon atoms and to be selected from alkyl or silyl radicals and carbonaceous groups attached to Z via the carbon of sp² hybridization an iminomethylenyl sequence

or of a —C(O)—N< sequence.

Preferably, $R_{10}$ is then of formula:

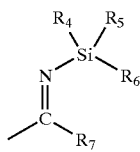

When $R_{10}$ is of formula (III):

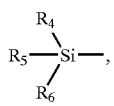

it is preferable for $R_{11}$ then to represent a negative charge or to be of formula (IV):

in which:

$R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si;

$R_7$ advantageously represents a hydrocarbonaceous radical of at most 30 carbon atoms, advantageously of aliphatic nature (that is to say, the carbon of which carrying the bond with the imine is of sp³ hybridization), in particular an alkyl radical, or advantageously an aryl, preferably isocyclic.

Thus, according to a preferred embodiment of the present invention, the compound (I) corresponds to either of the following formulae (Va) or (Vb):

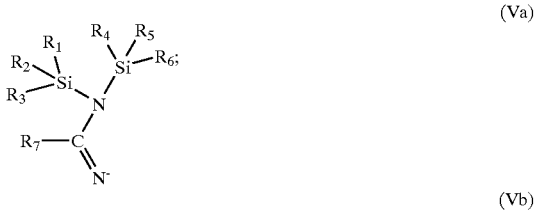

(Va)

(Vb)

These compounds can be obtained by the action of the anion of formula (1) on a nitrile ($R_7$—CN). The compound of formula (Va) is then obtained, which compound isomerizes to the compound of formula (Vb).

According to another advantageous embodiment of the invention, said compound of formula (I) is selected from the compounds of formulae (1) and (2):

(1)

(2)

where $R_1$, $R_2$, $R_3$, $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si.

Any cocation not carrying acidic hydrogen (that is to say, the pKa of which is less than 20 and better still less than 30) gives satisfactory results. To avoid oxidation/reduction side reactions, it is preferable but not essential for the cations to correspond to elements which, outside the elemental state, have only a single oxidation state. When they possess several oxidation states, it is preferable for them to be in the oxidation state of lowest valency.

Conventionally, however, preference is given, among said inorganic cations, to alkali metals with a rank at least equal to that of sodium. It is also possible to use organic cations having equivalent properties, such as, for example, onium fluorides (that is to say, in which the cations have a name formed by the addition of the onium suffix, such as sulfonium, phosphonium, ammonium, and the like) of the tetraalkylammonium, tetraalkylphosphonium or trialkylsulfonium type; or, more rarely, iniums (that is to say, in which the cations have a name formed by the addition of the inium suffix, such as sulfinium, phosphinium, iminium, and the like), such as pyridiniums.

These oniums are advantageously in the cations formed by the semimetal elements from Groups VB and VIB (as defined in the Periodic Table of the Elements published in the Supplement to the Bulletin de la Société Chimique de France in January 1966) with respectively 4 or 3 monovalent hydrocarbonaceous chains. It should be pointed out that oxoniums are not very stable and cannot be used in this application.

The iniums formed by the semimetal elements from Groups VB and VIB (as defined in the Periodic Table of the Elements published in the Supplement to the Bulletin de la Société Chimique de France in January 1966) with respectively 3 or 2 hydrocarbonaceous chains, one of which is bivalent and forms a double bond with said semimetal element and the others of which monovalent.

Preference is given, among these oniums, to the tetraalkylammoniums of 4 to 24 carbon atoms, preferably of 4 to 12 carbon atoms. The tetraalkylammonium is generally tetramethylammonium. And the tetraalkylphosphoniums.

The choice of said cocations can play a role in the distribution of the various (cyclo)condensates.

When they are selected from cations which promote the dissociated nature, such as iniums and in particular oniums, and from alkali metal cations, the distribution between the various entities is not very different from that obtained with HMDZ. On the other hand, the catalytic power is multiplied by a factor often of greater than 10.

Use may also be made of polyvalent cations, such as cations of alkaline earth metal compounds and rare earth metals, and in particular metals from the group of aluminum or silicon, and transition metals, these metals make possible better control of the kinetics.

Mention should in particular be made of the cations of rare earth metals, including cations of lanthanum and of lanthanide metals and in particular of erbium. Erbium, in particular as cation of the catalysts of formula (1) as defined above, gives compositions which are richer in a compound which is present only in the form of traces which are difficult to measure when trimerization techniques of the prior state of the art are used. They are also trimeric compounds but having a 6-amino-5-azauracil ring of formula:

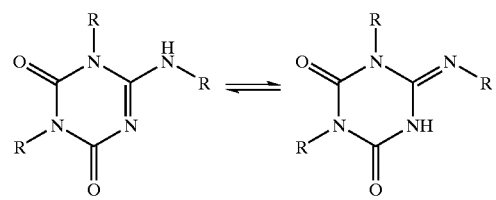

In this specific case, the content of this compound depends predominantly on the amount of catalyst used. The basicity of these products confers a particular advantage on them, alone or, preferably, in conventional isocyanate compositions, such as those known under the names of trimer or of biuret.

The R groups, which are identical or different, represent the residues of the monomer or monomers after discounting one of the isocyanate functional groups, it being possible for the others to be involved in a separate condensation.

The use of tin salts and in particular of tin(II) as cation of the compounds of formula (I) results in the predominant formation of IUT (2-imino-4-oxo-1,3-diazetidine) of formula:

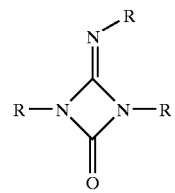

where the R groups, which are identical or different, represent the residues of the monomer or monomers after discounting one of the isocyanate functional groups, it being possible for the others to be involved in a separate condensation.

The basicity of these two types of above products confers a particular advantage on them, alone or, preferably, in conventional isocyanate prepolymer compositions, such as those known under the names of trimer or of biuret, this being the case at a level of at least 1% by mass, advantageously of at least 3%, preferably at least 5%. They are of use in particular in coatings, adhesives and microencapsulations.

As isocyanate prepolymer compositions comprising, in a mixture, either compounds with a 6-amino-5-azauracil unit or with a 2-imino-4-oxo-1,3-diazetidine unit, sometimes denoted by the abbreviation IUT (IminoUreTidinedione), are advantageously selected from those obtained by an oligocondensation of diisocyanate monomers, indeed even of triisocyanate monomers (preferably diisocyanate monomers), and optional removal of the residual monomers or by mixing two or more subcompositions of the above type and resulting from oligocondensation reaction carried out under distinct (temperature, catalyst) conditions.

It is desirable for these compositions to exhibit a mean functionality advantageously of greater than 2.5, preferably of greater than 3, preferably and advantageously at most equal to 8 and preferably to 6, more preferably to 4, comprising:

(a) from 0 to 20%, advantageously at least 0.5%, by mass with respect to the total mass of the components a), b) and c) of compounds carrying a single uretidinedione functional group; and for which the molecular mass is at most equal to three times the molecular mass of the monomer (or of the heaviest monomer, if there are several monomers) of said isocyanate monomers;

(b) from 0 to 65%, advantageously at least 10%, by mass with respect to the total mass of the components a), b) and c) of compounds carrying either a single isocyanurate unit or a single biuret unit and for which the molecular mass is at most equal to five times the molecular mass of the monomer (or of the heaviest monomer, if there are several monomers) of said isocyanate monomers;

(c) at least 15% and at most 60% by mass with respect to the total mass of the components a), b) and c) of a mixture of polyisocyanate compounds resulting from said monomer or monomers (that is to say, carrying at least 2 isocyanate functional groups) other than a) and b);

(d) at least 1%, advantageously 3%, by mass with respect to the mass of the components a), b), c) and d) of compounds carrying at least one isocyanate functional group and carrying at least one unit selected from 6-amino-5-azauracil and 2-imino-4-oxo-1,3-diazetidine;

(e) from 0 to 10% by mass with respect to the mass of the components a), b), c), d) and e) of impurities, including the starting monomers;

and (f) from 0 to 100%, advantageously from 0 to 70%, by mass with respect to the mass of the components a), b), c), d) and e) of a solvent (that is to say, inert with respect to the isocyanate) for which the boiling point at atmospheric pressure is advantageously at most equal to 200° C., preferably to 150° C.

In d), the compounds with a 6-amino-5-azauracil unit advantageously do not exceed 20%, preferably do not exceed 10%, of a), b), c) and d). On the other hand, the compounds with 2-imino4-oxo-1,3-diazetidine units can reach 90%, indeed even 95%, of a), b), c) and d). However, when the compounds with 2-imino-4-oxo-1,3-diazetidine units exceed 40%, the ratio by mass of compounds exhibiting more than one 2-imino-4-oxo-1,3-diazetidine unit of compounds to those comprising just one of them is then advantageously at least equal to ⅟₁₀.

Generally, a) represents at least 1% by mass with respect to the total mass of the components a), b) and c) and, according to an advantageous embodiment of the present invention, at least 5% and even at least 10%.

The components a)+b) advantageously represent at least 10%, preferably at least 20%, of components a), b) and c).

The components b)+d) advantageously represent at least 30%, preferably 40%, more preferably 50%, by mass of a), b), c) and d).

It is also advantageous for the compounds with 2-imino-4-oxo-1,3-diazetidine units to represent at least 20%, advantageously 30%, preferably at least 40%, of a), b), c) and d).

These compositions are advantageously based on a monomer selected from HDI, NBDI, IPDI and their mixtures.

The component (f) is advantageously at most equal to 5%, preferably to 3%.

The starting monomers advantageously represent at most 10%, preferably at most 2%, of the components a), b), c), d) and e).

The present invention is also targeted at compositions comprising, by successive or simultaneous addition:

an isocyanate composition exhibiting free or masked, advantageously aliphatic, isocyanate functional groups;

a saline compound according to the invention or a compound resulting from the addition of a saline compound according to the invention with an isocyanate functional group.

Said isocyanate composition advantageously comprises a monomer or a mixture of monomers as described subsequently.

The molar ratio of amount of catalyst (expressed as moles of anion of formula (I)) to amount of NCO functional groups (expressed as equivalent) is advantageously at least $10^{-5}$ and at most $5\times10^{-2}$, preferably within the closed range, that is to say comprising the limits, ranging from $10^{-4}$ to $10^{-3}$. It is advisable to select the alkali metals, alkaline earth metals, oniums and iniums in the lower part of the range, that is to say from $10^{-5}$ to $5\times10^{-3}$, advantageously from $5\times10^{-5}$ to $10^{-3}$, and, for the other cations, in the upper part of the range, that is to say from $10^{-4}$ to $5\times10^{-2}$, advantageously from $5\times10^{-4}$ to $5\times10^{-3}$.

When the isocyanate functional group to be (cyclo) condensed is a functional group carried by a non-neopentyl primary aliphatic radical, the maximum values above can be divided by a factor of five, indeed even of ten.

Another subject matter of the invention is a process for the catalytic (cyclo)condensation of isocyanate monomers which comprises:

a) the reaction of the starting isocyanate monomers with a catalyst comprising an inorganic or organic saline compound of a compound of formula (I) and in particular of formulae (1) and (2):

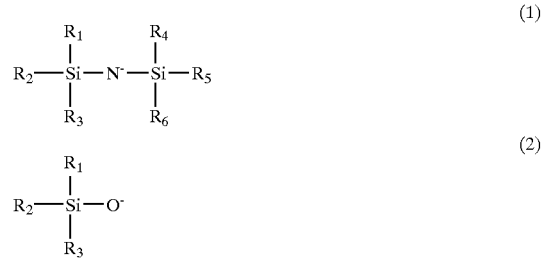

in which formulae the $R_1$, $R_2$, $R_3$, $R_4$, $R_5$ and $R_6$ symbols, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si.

In the formula (1), one of $R_1$, $R_2$, $R_3$, $R_4$, $R_5$ and $R_6$ represents a unit of formula:

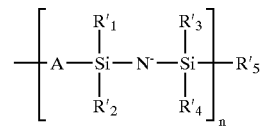

A being an alkylene chain having from 1 to 30 carbon atoms, advantageously from 2 to 20 carbon atoms, which is optionally substituted by one or more halogen atoms or CN or ester groups and/or is optionally interrupted by one or more atoms selected from O, S, N and Si, preferably $(CH_2)_{n'}$ with n' between 1 and 6, advantageously from 2 to 6, and $R'_1$ to $R'_5$, which are identical or different, representing a monovalent aliphatic, cycloaliphatic, which is saturated or unsaturated, aryl, aralkyl or alkylaryl group of hydrocarbonaceous nature which is optionally substituted by one or more halogen atoms or CN or ester groups and/or is optionally interrupted by one or more atoms selected from O, S, N and Si, and n is an integer between 1 and 50, or two from $R_1$, $R_2$ and $R_3$, on the one hand, and/or $R_4$, $R_5$ and $R_6$, on the other hand, together constitute a divalent hydrocarbonaceous group which is optionally substituted by one or more halogen atoms or CN or ester groups and/or is optionally interrupted by one or more atoms selected from O, S, N and Si, and/or at least one group selected from $R_1$, $R_2$ and $R_3$ forms, with at least one group from $R_4$, $R_5$ and $R_6$, a divalent hydrocarbonaceous group which is optionally substituted by one or more halogen atoms or CN or ester groups and/or is optionally interrupted by one or more atoms selected from O, S, N and Si, or a precursor of said compound, b) at a temperature of at least 20° C. and advantageously of at least 40° C. and of at most 200° C., advantageously of at most 150° C., c) the halting of the (cyclo)condensation reaction at the desired degree of conversion, advantageously of between 5 and 95%, preferably between 10 and 50%; and d) the optional removal of the unreacted monomers or the reaction with other compounds which react with the isocyanate functional group.

Advantageously, $R_1$ to $R_6$ and $R'_1$ to $R'_5$, which are identical or different, represent:

an alkyl, alkenyl, haloalkyl or haloalkenyl group having from 1 to 20, preferably from 1 to 6, carbon atoms which is optionally substituted by one or more chlorine and/or fluorine atoms and/or is optionally interrupted by one or more nitrogen and/or silicon atoms, a cycloalkyl, cycloalkenyl, halocycloalkyl or halocycloalkenyl group having from 3 to 30, preferably 3 to 10, carbon atoms and comprising chlorine and/or fluorine atoms and/or which is optionally interrupted by one or more nitrogen and/or silicon atoms, an aryl, alkylaryl or haloaryl group having from 6 to 30, preferably 6 to 10, carbon atoms and comprising chlorine and/or fluorine atoms, a cyanoalkyl group having from 1 to 6 carbon atoms, or two groups from $R_1$, $R_2$ and $R_3$ or $R_3$, $R_4$ and $R_5$ together form a divalent radical comprising from 2 to 5 carbon atoms and/or which is optionally interrupted by one or more nitrogen and/or silicon atoms, or two from $R_1$, $R_2$ and $R_3$, on the one hand, and/or $R_4$, $R_5$ and $R_6$, on the other hand, together constitute a divalent hydrocarbonaceous group and/or which is optionally interrupted by one or more nitrogen and/or silicon atoms, or at least one group selected from $R_1$, $R_2$ and $R_3$ forms, with at least one group from $R_4$, $R_5$ and $R_6$, a divalent hydrocarbonaceous group comprising from 2 to 5 carbon atoms and/or which is optionally interrupted by one or more nitrogen and/or silicon atoms.

Preferably, $R_1$ to $R_6$, which are identical or different, are selected from methyl, ethyl, propyl, isopropyl, butyl, isobutyl, α-pentyl, t-butyl, chloromethyl, dichloromethyl, α-chloroethyl, α,β-dichloroethyl, fluoromethyl, difluoromethyl, α,β-difluoroethyl, 3,3,3-trifluoropropyl, trifluorocyclopropyl, 4,4,4-trifluorobutyl, 3,3,3,4,4,5,5-heptafluoropentyl, β-cyanoethyl, γ-cyano-propyl, phenyl, p-chlorophenyl, m-chlorophenyl, 3,5-dichlorophenyl, trichlorophenyl, tetrachlorophenyl, o-, p- or m-tolyl, α,α,α-trifluorotolyl and xylyl (2,3-dimethylphenyl; 3,4-dimethylphenyl) groups;

or two groups from $R_1$, $R_2$ and $R_3$, on the one hand, and/or $R_4$, $R_5$ and $R_6$, on the other hand, taken together, represent an ethylene, propylene, butylene or pentylene group, preferably their linear isomers, a trimethylene, tetramethylene or pentamethylene group or an —N⁻—Si(CH$_3$)$_2$—N⁻— group;

and/or $R_1$ and $R_4$, taken together, represent a group selected from ethylene, propylene, butylene, pentylene, preferably the unbranched isomers, dimethylene and trimethylene.

Particularly preferred $R_1$ to $R_6$ and $R'_1$ to $R'_5$ groups are selected from methyl, ethyl, propyl, which are linear or branched, if appropriate, vinyl and phenyl, which can optionally be chlorinated and/or fluorinated. The case of vinyl is advantageous insofar as this type of compound can make possible the polymerization or the copolymerization with other ethylenic monomer and thus makes possible the insertion of the catalyst unit (in particular the units of formulae (1), (2), (Va) and (Vb), where at least one of the $R_1$ to $R_6$ groups provides the connection with the polymer) in a polymer network.

When the $R_1$ to $R_6$ and $R'_1$ to $R'_5$ groups are chlorinated and/or fluorinated, the number of halogen atoms varies from 1 to all the available valencies.

Mention may very particularly be made of the salts of the following silazane compounds:

hexamethyldisilazane, 1,3-diethyl-1,1,3,3-tetramethyldisilazane, 1,3-divinyl-1,1,3,3-tetramethyldisilazane, hexaethyldisilazane, 1,3-diphenyl-1,1,3,3-tetramethyldisilazane, hexamethylcyclotrisilazane, and 2,5-ethylene-2,2,5,5-tetramethylcyclodisilazane.

Mention may also be made of the following silanolates:

trimethylsilanolate, triethylsilanolate, ethyldimethylsilanolate, vinyldimethylsilanolate.

The salt of the compound of formulae (I), in particular (1), (2), (Va) or (Vb), can be a monovalent or multivalent inorganic salt or a mixture of these salts.

The preferred inorganic salts, advantageously well dissociated, are alkali metals and alkaline earth metals, in particular those of K, Li, Na and Mg.

The salt of the compound of formula (I), in particular (1), (2), (Va) or (Vb), can also be a monovalent or multivalent organic salt or a mixture of these salts. The preferred organic salts are stable "oniums" or "iniums".

According to an advantageous alternative of the invention, the salt of the compound of formula (I) is an erbium salt of the compound of formula (1) and it is preferable in this case for all the ligands to be erbium salts of the compound of formula (1). These correspond to the following general formula ($1^E$) when n' represents zero:

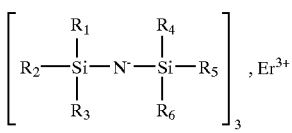

(1<sup>E</sup>)

Mention may very particularly be made of the erbium salts of the following compounds:
hexamethyldisilazane,
1,3-diethyl-1,1,3,3-tetramethyldisilazane,
1,3-divinyl-1,1,3,3-tetramethyldisilazane,
hexaethyldisilazane, and
1,3-diphenyl-1,1,3,3-tetramethyldisilazane.

According to another advantageous alternative of the invention, the salt of the compound of formula (I) is a tin(II) salt of the compound of formula (1) and it is preferable in this case for all the ligands to be tin salts of the compound of formula (1). These correspond to the following general formula ($1^S$) when n' represents zero:

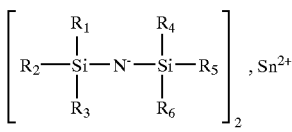

($1^S$)

Mention may very particularly be made of the tin(II) salts of the following compounds:
hexamethyldisilazane,
1,3-diethyl-1,1,3,3-tetramethyldisilazane,
1,3-divinyl-1,1,3,3-tetramethyldisilazane,
hexaethyldisilazane,
1,3-diphenyl-1,1,3,3-tetramethyldisilazane,
hexamethylcyclotrisilazane, and
2,5-ethylene-2,2,5,5-tetramethylcyclodisilazane.

In the case of multivalent cations, the salt according to the invention can comprise at least one above anion, often acting as coordinant (or ligand), of formula (I), in particular (1), (2), (Va) or (Vb), and optionally one or more different anions, often acting as coordinants (or ligands).

It is generally preferable for all the anions, often acting as coordinants (or ligands), to be compounds of formula (1) or (2).

The number of the anions, often acting as coordinants (or ligands), depends on the valency of the inorganic or organic cation and on the number of nitrogen atoms in the compound of formula (1).

The oniums are selected from the group of cations formed by the elements from Groups VB and VIB (as defined in the Periodic Table of the Elements published in the Supplement to the Bulletin de la Société Chimique de France in January 1966) with 4 (case of Group VB) or 3 (case of Group VIB) hydrocarbonaceous chains.

The organic salt of the invention is in this case advantageously a phosphonium, sulfonium or ammonium.

The iniums, to which group the pyridiniums belong, derive from the oniums by replacement of two substitutents by a doubly-bonded substitutent.

It is also possible to have a mixture of inorganic and organic salts.

The silazane salts of the invention are known compounds which are commercially available or can be easily prepared from the corresponding silazanes, for example by reaction with a metal amide or hydride, such as LiH, NaH, NaNH$_2$ or KH or an alkylmetal, for example butyllithium, in ether medium at ambient temperature.

The salts of the invention can also be obtained by exchange of the lithium cation of a lithium salt with a cation of a heavy metal, for example erbium or tin, using the corresponding chloride, for example erbium chloride or tin chloride.

The starting silazanes are known compounds which are commercially available or can be obtained from the corresponding chlorosilazanes by means of simple reactions which are conventional in the field in question.

Reference may be made, for the preparation of cyclic silazanes, to Houben-Weyl, *Methoden der Organischen Chemie: "Organosilicum Verbindungen"* [Methods of Organic Chemistry: "Organosilicon Compounds"], Georg Thieme Verlag, Stuttgart (1980).

For further information regarding the preparation of silazane salts, reference may be made to the same work or to the methods described in *Organomet. Chem.*, (1983), 461(1–2), 75–80; *Chem. Prum.*, (1977), 27(11), 566–8; *Zh. Obstich. Khim.*, (1988), 58(8), 934–5; *Inorg. Synth.*, (1966), 8, 19–22 or *Inorg. Chem.*, (1966), 8, 15–19.

The silanolates of the invention are known compounds which are commercially available or can be obtained from the corresponding chlorosilanes in a basic medium or by exchange of the Li$^+$ cation with a salt of a heavy metal, such as erbium or tin, for example.

When the compound of formula (I), in particular (1), (2), (Va) or (Vb), is formed in situ, the starting material is a precursor of said compound which is released by means known per se to form the corresponding active compound.

In stage c), the other compounds reactive with the isocyanate functional group can be isocyanates or compounds carrying a mobile hydrogen atom, in particular amines, alcohols, imidazoles, pyrazoles, malonates, and the like, which are substituted or unsubstituted.

Thus, the 2-imino-4-oxo-1,3-diazetine (IUT) compounds, obtained during the use of the tin(II) salts in the process according to the invention, result, in the presence of hydrochloric acid, by reaction with an isocyanate compound, in particular in which the isocyanate functional group is carried by a carbon atom belonging to an aromatic ring, in asymmetric derivatives with a 4,6-dioxo-2-imino-hexahydro-1,3,5-triazine ring of formula:

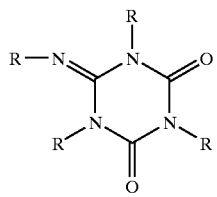

in which R is as defined for the compounds with the above IUT structure.

The catalysts of the invention are suitable for the the oligo- and for the polycondensation, in particular the oligomerization and especially the (cyclo)trimerization, of aliphatic, which are linear or branched, in particular in the α or β position, cycloaliphatic or aromatic isocyanates.

The present invention is targeted at the oligomerization, in particular the trimerization, of isocyanate compounds generally and preferably carrying two isocyanate functional groups, denoted in the present description by isocyanate monomers.

They can be isocyanate monomers with a hydrocarbonaceous backbone exclusively of linear, branched or cyclic aliphatic nature or aromatic isocyanates.

Mention may in particular be made, as aliphatic monomer (that is to say, the carbon of which carrying the nitrogen of the isocyanate functional group is of $sp^3$ hybridization), of non-neopentyl primaries and more particularly true linears, such as hexamethylene diisocyanate (HDI) and tetramethylene diisocyanate.

Mention may also be made of aliphatic monomers in which the hydrocarbonaceous backbone is branched but in which the isocyanate functional groups are carried by primary carbon atoms, for example 2-methylpentane diisocyanate.

Mention may also be made of monomers in which at least one isocyanate functional group is in the secondary, in particular cycloaliphatic, tertiary or neopentyl position. However, these isocyanate functional groups are generally less reactive than the primary isocyanate functional groups and require, when the cocations are cations which do not facilitate the dissociation and in particular when they are di- or polyvalent, severe conditions (higher content of catalyst, and temperature higher by at least 20° C. and even by 30° C., indeed even 40° C.).

Thus, among these products, those which give excellent results with the catalysts of the invention, unlike the other catalysts with which they have only a mediocre degree of conversion, are the monomers in which the isocyanate functional group is carried by a secondary, tertiary or neopentyl cycloaliphatic carbon atom, in particular cycloaliphatic isocyanates. These monomers are such that at least one advantageously of the two isocyanate functional groups is distant from the closest ring by at most one carbon and is preferably connected directly to it. In addition, these cycloaliphatic monomers advantageously exhibit at least one, preferably two, isocyanate functional groups selected from secondary, tertiary or neopentyl isocyanate functional groups.

Surprisingly, good results are obtained for isocyanates in which the conformational freedom of the carbon carrying the NCO functional group is low. Mention may be made, by way of example, of the following monomers:

compounds corresponding to the hydrogenation of the aromatic nucleus or nuclei carrying isocyanate functional groups of aromatic isocyanate monomers and in particular of TDI (toluene diisocyanate) and diisocyanatobiphenyls, the compound known under the abbreviation $H_{12}MDI$ (4,4'-bis(isocyanatocyclohexyl)methane), the various BIC [bis(isocyanatomethylcyclohexane)] compounds and cyclohexyl diisocyanates, which are optionally substituted;

and in particular norbornane diisocyanate, often denoted by its abbreviation NBDI;

isophorone diisocyanate or IPDI or more specifically 3-isocyanatomethyl-3,5,5-trimethylcyclohexyl isocyanate.

Mention may be made, as aromatic monomers, of:

2,4- or 2,6-toluene diisocyanate (TDI);
2,6-4,4'-diphenylmethane diisocyanate (MDI);
1,5-naphthalene diisocyanate (NDI);
tolidine diisocyanate (TODI);
p-phenylene diisocyanate (PPDI).

The starting monomers can also be oligomerization products of isocyanates of lower molar mass, these oligomerization products carrying isocyanate functional groups. In this case, it is not necessary to separate the unconverted oligomer from the reaction product formed on conclusion of the trimerization reaction.

The catalyst is preferably used as is or dissolved in an inert solvent before introduction into the reaction medium. The solvent for formulation of the catalyst is preferably inert with respect to the isocyanates of the reaction medium. In the case where the solvent is reactive with respect to the isocyanates, the concentration of the catalyst is adjusted so that the amount of solvent is not harmful to the production of the compound of the targeted application.

The solvent is preferably chosen so that its boiling point is greater than the reaction temperature. Mention may be made of aliphatic hydrocarbons, such as hexane, or aromatic hydrocarbons, such as toluene.

However, it is possible to operate under pressure with solvents or gases in the supercritical state.

The amount of catalyst varies as a function of the nature of the metal cation of the silazane salt and of the starting isocyanate.

Thus, the reactivity of the silazane salts follows the following order:

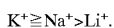

The molar ratio of amount of catalyst to amount of NCO functional groups is advantageously at least $5 \times 10^{-5}$ and at most $5 \times 10^{-3}$, preferably between $10^{-4}$ and $10^{-3}$.

The amount of catalyst is advantageously from approximately 0.01 to 0.07%, with respect to the weight of the cation.

When the gases dissolved in the starting isocyanate monomers are removed, the amount of catalyst can be reduced.

In addition, when the gases dissolved in the starting isocyanate monomers are removed, the reactivity of the catalysts is improved.

The dissolved gases ($CO_2$, halogenated gas, $O_2$, and the like) can be removed by any known means, in particular by sparging with an inert gas, such as nitrogen or argon, or by placing the reaction medium under vacuum.

The amount of catalyst will therefore be chosen according to the kinetics of reaction and the physicochemical properties (viscosity, and the like) expected, excessively low amounts not making possible the production of trimers in a significant amount but giving products of low viscosity with a high level of true trimers (a single isocyanurate unit). Conversely, there is a risk of reaction runaway with excessively high amounts.

The reaction temperature is at least 20° C., advantageously at least 30° C.

As soon as the reaction begins, it is exothermic. It is therefore generally preferable to control the temperature of the reaction medium in order to prevent a reaction runaway liable to result in uncontrolled polymerization of the isocyanate.

It is generally preferable to gradually introduce the dilute catalyst, for example by running in slowly.

In some cases, when seeking to obtain compounds, in particular (cyclo)trimers, with a urea or biuret functional group, it is possible to be induced to add water to the reaction medium.

However, it had been observed that the water added resulted in a slowing of the kinetics of (cyclo)condensation, in particular of (cyclo)trimerization.

The polycondensation reaction is halted at the desired degree of conversion, generally between 5% and 95%, advantageously between 8% and 60%, of the NCO functional groups, by addition of a deactivator of the catalyst or by removing the latter by any means known to persons skilled in the art, such as column absorption, and the like.

It is possible in particular to halt the reaction by addition of an acid compound (for example, an amine salt) or a compound or a mixture of compounds which can generate, in the reaction medium, an acid compound capable of neutralizing the activity of the catalyst, in particular an acid salt.

During the study which led to the present invention, it was shown that it was preferable to add a strong acid, generally having a pKa≦3, such as sulfuric or sulfonic acids, for example mesylic, tosylic or halosulfonic acids, or a phosphoric acid, or phosphonic of higher pKa, preferably a phosphorus-comprising acid ester.

Mention may be made, as phosphorus-comprising acid esters, of phosphate esters, in particular monoesters, diesters or their mixtures.

Mention may be made of phosphonates, preferably monoesterified phosphonates, and phosphinates.

Mention may also be made of inorganic acids, preferably halogenated inorganic acids, for example HF, HCl or HBr.

However, the poisoning of the catalyst is preferably carried out by means of acid esters of phosphoric acid and in particular dialkyl phosphates, in particular dibutyl phosphate and di(2-ethylhexyl) phosphate.

It is also possible to use precursor compounds of an acid compound, such as Lewis acids (AlCl$_3$, ZnCl$_2$) or metal triflates.

The reaction product comprises polycondensation products, in particular (cyclo)condensation products, of the starting isocyanates.

They are mainly, indeed even exclusively, compounds with an isocyanurate ring, in particular "true" trimers having a single isocyanurate ring, in particular when the cation is an organic cation of the type described above or an inorganic cation, such as K$^+$, Na$^+$ or Li$^+$.

They can also be trimeric compounds having a ring other than the isocyanurate. For example, when the cation of the compound of formula (I) employed is erbium, the trimers obtained in the (cyclo)condensation reaction can comprise a 6-amino-5-azauracil ring of formula:

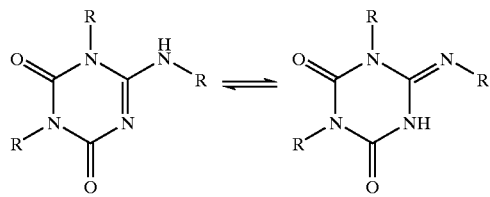

in which R represents the residue of a compound with an isocyanate functional group after removal of said isocyanate functional group.

On conclusion of the process as defined above and when tin, in particular tin(II), salts are used as cations of the compounds of formula (I), it is possible to obtain a composition mainly comprising, in addition to the unreacted starting isocyanate monomers, dimeric compounds, in particular cyclodimers. The cyclodimers obtained have a single ring with a 2-imino-4-oxo-1,3-diazetidine (IUT) structure of formula:

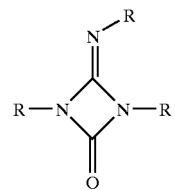

in which R is the residue of an isocyanate monomer compound of formula R—N—CO, in which R is in particular a linear or branched aliphatic, cycloaliphatic or aromatic hydrocarbonaceous residue having from 4 to 30 carbon atoms optionally comprising one or more substituents selected from an NCO group, a carbamate, allophanate, ester or ether group, and the like.

They can also be oligomeric compounds having two, indeed even more than two, 2-imino-4-oxo-1,3-diazetidine (IUT) rings.

Such compounds comprising a 2-imino-4-oxo-1,3-diazetidine ring are already known, in particular for having been prepared by a cycloaddition (2+2) of isocyanates to carbodiimides (Houben Weyl, *Methoden der Organischen Chemie* [Methods of Organic Chemistry], 4th edition, Georg Thieme Verlag, (1983), 1111–1113).

The presence of a substantial content of compounds of IUT structure in a polyisocyanate composition is particularly advantageous insofar as these compounds have an NCO functionality of 3 and a lower mass in comparison with the corresponding monoisocyanurates with the same functionality.

Generally, when the process according to the invention is employed and according to the degree of conversion, the final mixture can additionally comprise heavy compounds with a high molecular weight.

Another subject matter of the invention is an isocyanate composition capable of being obtained by the process as defined above.

This composition is characterized in particular in that it comprises less than 1% by weight of isocyanate monomers with respect to the total weight of the isocyanate compounds present in the composition. It can advantageously be characterized in that the concentration of free isocyanate functional group is between 0.5 and 7 equivalents per liter.

Furthermore, the isocyanate composition according to the invention comprises, by mass, at least 1%, advantageously at least 3%, preferably at least 5%, of compound exhibiting at least one unit:

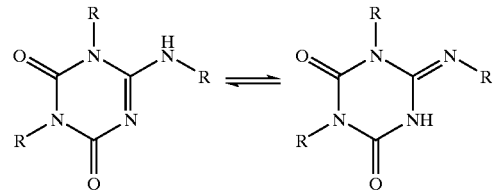

where the R groups, which are identical or different, represent the residues of the monomer or monomers after discounting one of the isocyanate functional groups, it being possible for the others to be involved in a separate condensation.

According to another aspect, the isocyanate composition according to the invention comprises, by mass, at least 1%, advantageously at least 3%, preferably at least 5%, of compound exhibiting at least one unit:

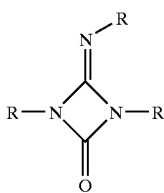

where the R groups, which are identical or different, represent the residues of the monomer or monomers after discounting one of the isocyanate functional groups, it being possible for the others to be involved in a separate condensation.

In particular, when the process has been carried out with erbium salts, the composition is characterized in that it advantageously comprises:

from 50 to 80% by weight of trimeric compounds composed of monoisocyanates and 6-amino-5-azauracils, from 0.5 to 5%, advantageously from 0.5 to 3%, of monouretidinedione compounds, less than 1% by weight of isocyanate monomers, with respect to the total weight of the isocyanate compounds present in the composition.

In the same way, when the process is carried out with tin salts, the composition is characterized in that it advantageously comprises:

from 50 to 75%, advantageously from 55 to 70%, by weight of mono-2-imino-4-oxo-1,3-diazetidine compounds;

from 10 to 25% by weight, advantageously from 12 to 20% by weight, of bis(2-imino-4-oxo-1,3-diazetidine) compounds;

from 10 to 25%, advantageously from 14 to 20%, by weight of isocyanate-urea; and less than 1% by weight of isocyanate monomers, with respect to the total weight of the isocyanate compounds present in the composition.

Another subject matter of the invention is a masked polyisocyanate composition, characterized in that it comprises less than 1% by weight of isocyanate monomers with respect to the total weight of the isocyanate compounds present in the composition, said composition comprising from 0.5 to 100%, advantageously from 10 to 100%, preferably from 20 to 100%, of isocyanate functional groups masked using an agent which masks the isocyanate functional group.

In particular, when the process has been carried out with erbium salts, the masked polyisocyanate composition is characterized in that it advantageously comprises:

from 50 to 80% by weight of trimeric compounds composed of monoisocyanates and 6-amino-5-azauracils, from 0.5 to 5%, advantageously from 0.5 to 3%, of monouretidinedione compounds, less than 1% by weight of isocyanate monomers, with respect to the total weight of the isocyanate compounds present in the composition, said composition comprising from 0.5 to 100%, advantageously from 10 to 100%, preferably from 20 to 100%, of isocyanate functional groups masked using an agent for masking the isocyanate functional group.

In the same way, when the process is carried out with tin salts, the masked polyisocyanate composition is characterized in that it advantageously comprises:

from 50 to 75%, advantageously from 55 to 70%, by weight of mono-2-imino-4-oxo-1,3-diazetidine compounds;

from 10 to 25% by weight, advantageously from 12 to 20% by weight, of bis(2-imino-4-oxo-1,3-diazetidine) compound;

from 10 to 25%, advantageously from 14 to 20%, by weight of isocyanate-urea; and less than 1% by weight of isocyanate monomers, with respect to the total weight of the isocyanate compounds present in the composition, said composition comprising from 0.5 to 100%, advantageously from 10 to 100%, preferably from 20 to 100%, of isocyanate functional groups masked using an agent which masks the isocyanate functional group.

The masking agent, which can be a mixture of masking agents, generally exhibits at least one mobile hydrogen, so that the masking reaction can be written:

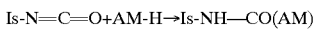

where AM-H represents the masking agent, AM- represents the masking group and Is is the residue carrying the isocyanate functional group under consideration, in particular of a composition as defined above.

Said masking agent exhibits at least one functional group carrying a mobile hydrogen or more specifically a reactive hydrogen, for which functional group it is possible to define a pKa which corresponds either to the ionization of an acid, including the hydrogen of the phenol and alcohol functional groups, or to the associated acid of a base, generally a nitrogenous base. The pKa of the functional group exhibiting hydrogens is at least equal to 4, advantageously to 5, preferably to 6, and is at most equal to 14, advantageously to 13, preferably to 12 and more preferably to 10, an exception having to be made for lactams, the pKa of which is greater than these values and which constitute masking agents which are nevertheless acceptable although not preferred for the invention. The masking agent advantageously comprises only a single mobile hydrogen.

Mention may be made, as nonlimiting examples of the masking agents according to the invention, of hydroxylamine derivatives, such as hydroxysuccinimide, and oximes, such as methyl ethyl ketoxime, phenol derivatives or the like, amide derivatives, such as imides and lactams, in addition to malonates or ketoesters and hydroxamates.

Mention may also be made of nitrogenous heterocyclic groups comprising 2 to 9 carbon atoms and, in addition to the nitrogen atom, from 1 to 3 other heteroatoms selected from nitrogen, oxygen and sulfur. Preference is given in particular to heterocycles comprising from 2 to 4 carbon atoms and from 1 to 3 nitrogen atoms, such as pyrrolyl, 2H-pyrrolyl, imidazolyl, pyrimidinyl, pyridazinyl, pyrazinyl, pyrimidinyl, pyridazinyl, indolizinyl, isoindolyl, indolyl, indolyl, indazolyl, purinyl, quinolizinyl, isoquinolyl, pyrazolidinyl, imidazolidinyl and triazolyl groups, these groups optionally being substituted by one to three substituents chosen from $NH_2$, $NH(C_1$–$C_6$ alkyl), $N(di(C_1$–$C_6$ alkyl)), OH, SH, $CF_3$, $C_1$–$C_6$ alkyl, $C_3$–$C_6$ cycloalkyl, $C_5$–$C_{12}$ aryl, in particular phenyl, $C_6$–$C_{18}$ aralkyl having from 5 to 12 carbon atoms in the aryl group, in particular benzyl, or $C_6$–$C_{18}$ alkylaryl having from 5 to 12 carbon atoms in the aryl group.

Reference may be made, for the determination of the pKa values, to "The determination of ionization constants, a laboratory manual", A. Albert and E. P. Serjeant, Chapman and Hall Ltd, London. Reference may be made, for the list of the blocking agents, to Z. Wicks (Prog. Org, Chem., (1975), 3, 73, and Prog. Org. Chem., (1989), 9,7) and Petersen (Justus Liebigs Annalen der Chemie, (1949), 562, 205).

The masked polyisocyanate compositions according to the invention are obtained by reaction of the product from stage c) or d) with a masking agent as defined above under the usual conditions.

When the masking agent is reacted with the product from stage c), it is opportune to carry out a stage d) for removal of the masked isocyanate monomers, if appropriate on conclusion of the masking stage proper.

The compositions according to the invention exhibit the advantage of comprising oligomers (in particular dimers and trimers) of isocyanates, the effect of which is to substantially lower the viscosity of the final composition.

The compositions thus obtained additionally exhibit the advantage of a faster drying when they are used for the preparation of coatings, in particular of paints or varnishes.

The compositions according to the invention are advantageously used as curing agent for coating compositions, in particular for paints or varnishes, by reaction of the free isocyanate functional groups, or isocyanate functional groups released by departure of the masking agent, with a compound which reacts with the multifunctional isocyanate bond, in particular a polyol.

The compositions according to the invention can also be used in adhesives or for the microencapsulation of encapsulatable active materials, in particular inks, biocides, detergents, and the like.

The following examples are intended to illustrate the invention. Unless otherwise indicated, the percentages are expressed by weight.

EXAMPLE 1

500 g of IPDI are placed with stirring in a 1 L jacketed reactor equipped with a stirrer, a reflux condenser, a heating device and a Huber bath by regulating the temperature. The reaction medium is heated to 60° C. 5 mL of 0.5 M potassium bis(trimethylsilyl)amide in toluene are added, representing an amount of catalyst of 0.1%.

The reaction medium turns slightly yellow in color.

A strong exotherm occurs. The temperature rises to 107° C. after 7 minutes.

At the end of the exotherm, 2 mL of dibutyl phosphate are added. The reaction medium immediately decolorizes and the trimerization reaction is halted.

The degree of conversion of the IPDI is 68.7%.

EXAMPLE 2

Example 1 is repeated but while changing the amount of catalyst (0.1 g).

No exothem occurs.

A further 1 mL of catalyst is added after reacting for 14.5 hours. The total amount of catalyst is 0.04%.

A slight exotherm then occurs. The reaction medium becomes tinged with yellow.

The reaction is halted after 3 hours by addition of 2 ml of dibutyl phosphate at 20° C. The degree of conversion of the IPDI is 8.2%.

EXAMPLE 3

Example 1 is repeated while sparging argon into the reaction medium before the addition of the catalyst.

The amount of catalyst added is 1.6 mL (0.04%).

The exotherm comes to an end 10 minutes after the beginning of the reaction (temperature: 75° C.).

0.17 g of dibutyl phosphate (0.5M solution in toluene) is added 30 minutes after the beginning of the addition of the catalyst. A significant decolorization of the reaction medium occurs. The degree of conversion of the IPDI is 51.7%.

EXAMPLE 4

The reaction is carried out as in example 3 except that the amount of IPDI is 400 g and the amount of catalyst added is 0.03% (1.2 mL of a 0.5M solution in toluene). The temperature rises to 150° C. after 4 minutes.

0.13 g of dibutyl phosphate is added 30 minutes after the end of the exotherm. A partial decolorization of the reaction medium occurs. The degree of conversion of the IPDI is 57.7%.

EXAMPLE 5

The reaction is carried out as in example 3, except that 400 g of IPDI are charged to the reactor and 1.2 mL of catalyst (0.03% by weight) are added. The temperature of the reaction medium rises to 150° C. after 3 minutes. The reaction is halted 1.5 hours after the addition of the catalyst by addition of 0.13 g of dibutyl phosphate. A slight decolorization of the reaction medium is observed.

EXAMPLE 6

The reaction is carried out as in example 1, except that the reactor is charged with 200 g of IPDI, and 6 mL of a 1M solution of lithium bis(trimethylsilyl)amide in hexane are added, which corresponds to 0.5% by weight of catalyst in the reaction medium.

The temperature of the reaction is 60° C. The reaction is halted after 4 hours by additions of 1.5 g of dibutyl phosphate. The degree of conversion of the IPDI is 32.3%.

EXAMPLE 7

Example 1 is repeated with 200 g of IPDI and 0.4% of lithium salt of HMDZ (1M solution in hexane).

The temperature of the reaction is 60° C. The reaction is halted after 2 hours by addition of 1 g of dibutyl phosphate. A partial decolorization is observed. The degree of conversion of the IPDI is 29.6%.

EXAMPLE 8

The reaction is carried out as in example 3 while charging the reactor with 263.8 g of HDI and while adding 0.53 mL of potassium salt of HMDZ (0.5M solution in toluene). The temperature of the reaction medium rises to 60° C. After reacting for 1 hour, the reaction medium is heated to 90° C. The reaction is halted after 3.25 hours by addition of 1 mL of dibutyl phosphate.

The degree of conversion of the HDI is 23.6%.

The IR spectrum corresponds to that of an HDI isocyanurate (1 463 cm$^{-1}$ and 1 684 cm$^{-1}$).

EXAMPLE 9

Example 1 is repeated while charging the reactor with 20 g of IPDI and while replacing the catalyst with lithium trimethylsilanolate (1 g). The temperature of the reaction medium is 60° C. The reaction is halted by addition of dibutyl phosphate (0.01 mol).

The degree of conversion of the IPDI is 72%.

The results of the tests are summarized in the table below.

TABLE

| Product/Component | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| IPDI (%) | 39.3 | 91.5 | 53.0 | 45.4 | 49.1 | 67.8 | 73.7 | — | 28.0 |
| HDI | | | | | | | | 76.4 | |
| Catalyst[1] | K, HMDZ (0.1) | K, HMDZ (0.04) | K, HMDZ (0.04) | K, HMDZ (0.03) | K, HMDZ (0.03) | Li, HMDZ (0.5) | Li, HMDZ (0.4) | K, HMDZ (0.04) | Li 8(Me)$_3$SiO (5) |
| Temperature | 60° C. | 60° C. | 60° C. | 120° C. | 150° C. | 60° C. | 60° C. | 90° C. | 60° C. |
| Argon sparging | No | No | Yes | Yes | Yes | No | No | Yes | No |
| Trimer + dimer (%) | 33.1 | 5.6 | 27.7 | 33.9 | 33.8 | 20.1 | 16.4 | — | 37.9 |
| Bis-trimer (%) | 15.9 | 2.1 | 12.4 | 13.7 | 11.8 | 8.6 | 7.0 | — | 20.9 |
| Heavy products (tris-trimer) (%) | 11.7 | 0.8 | 6.9 | 7.0 | 5.2 | 3.5 | 2.9 | | 13.2 |

[1]% by weight with respect to the weight of isocyanate

EXAMPLE 10

20 g (0.09 mol, 0.18 mol of NCO) of IPDI are placed with stirring in a 50 mL jacketed reactor equipped with a stirrer, a reflux condenser, a heating device and a Huber bath by regulating the temperature. The reaction medium is heated at 60° C. 1 g (MW=648) of erbium [tris(trimethylsilyl)]amide is added, representing an amount of catalyst of 5% by weight with respect to the weight of the IPDI with respect to the metal ($1.5 \times 10^{-3}$ mol of catalyst).

After five hours, 300 mg of dibutyl phosphate are added. Halting of the trimerization reaction occurs. The degree of conversion of the IPDI is 23.2%.

The results of the test are summarized in the table below:

| Product/Component | % by weight with respect to the weight of isocyanate |
|---|---|
| IPDI (%) | 76.8% |
| IPDI Trimethylsilylurea | 2.0% |
| True dimer (monouretidinedione) | Trace |
| Unidentified urea or diurea | |
| Trimer (+ azauracil + biuret) | 15.9% |
| Heavy products | 5.4% |

EXAMPLE 11

20 g (0.09 mol, 0.18 mol of NCO) of IPDI are placed with stirring in a 50 mL jacketed reactor equipped with a stirrer, a reflux condenser, a heating device and a Huber bath by regulating the temperature. The reaction medium is heated to 60° C. 1 g ($2.275 \times 10^{-3}$ mol) of tin [tris(trimethylsilyl)] amide is added, representing an amount of catalyst of 5% by weight with respect to the weight of the starting IPDI.

After reacting for 5 hours at 60° C., 300 mg of dibutyl phosphate are added. Halting of the reaction occurs.

The degree of conversion of the IPDI is 26.5%.

The results of the test are summarized in the table below:

| Product/Component | % by weight with respect to the weight of isocyanate |
|---|---|
| IPDI (%) | 74.5% |
| IPDI Trimethylsilylurea | 4.7%* |
| IUT** | 16.3% |
| Bis-IUT | 4.3% |

*Presence of carbodiimide functional groups
**2-imino-4-oxo-1,3-diazetidine

EXAMPLE 12

Cyclotrimerization of the HDI (Hexamethylene Diisocyanate) Monomer

Procedure

After introducing 10 mg of catalyst into a two-necked round-bottomed flask in a glove box, the monomer is added. Only a partial dissolution of the catalyst is observed. The reaction mixture is left stirring for 5 hours at 60° C.

In order to facilitate the homogenization of the reaction medium, a second test is carried out in which the catalyst is dissolved in 0.5 mL of toluene before addition of the monomer. The mixture appears homogeneous. Under special instruction, the reaction is carried out for 5 hours at 60° C.

An IR analysis of the reaction mixtures after the tests is subsequently carried out.

| Catalyst | Percent by mass | Solvent | Appearance of the crude product | Trimer bands observed in cm$^{-1}$ |
|---|---|---|---|---|
| Y(N(SiMe$_3$)$_2$)$_3$ | 1% | No | Off-white paste and opaque solid | 1690 1464.5 |
| Y(N(SiMe$_3$)$_2$)$_3$ | 1% | Yes | Off-white paste | 1686 1466.5 |

The interpretation of the spectra indicates that the trimerization of the monomer indeed takes place. These operating conditions are thus used. However, the catalyst is dissolved in toluene to retain a homogeneous concentration of the catalyst in the reaction mixture.

EXAMPLE 13

Comparison Between the Yttrium Complex and NaN(SiMe$_3$)$_2$

A new test is carried out in which the lanthanide complex is replaced by the corresponding salt. A main insoluble opaque part and an off-white liquid paste are obtained. IR analysis illustrates the presence of trimer in both fractions but the bands characteristic of the trimer for the soluble part are weak. GPC/FTIR analysis also indicates the presence of trimer but also bis-trimer, of tris-trimer and of heavy compounds with isocyanate functional groups. As the reaction mixtures are not completely soluble, a quantitative analysis can not be carried out. The silylamide salt thus makes possible trimerization but the trimerization has gone much further.

EXAMPLE 14

Study of Parameters

An attempt is made to determine the influence of the nature of the metal center of the catalyst, of the amount of catalyst and of the temperature of the reaction medium on the trimerization of the monomer. Analysis by GPC coupled to FTIR makes it possible to determine the nature of the entities present, to quantify them and to determine the overall degree of conversion (Ov) and the degree of conversion of a monomer to trimer (T).

Influence of the Nature of the Metal Center

| Metal center | Appearance of the RM | Trimer bands in cm$^{-1}$ | Entities present (GPC/FTIR analysis) | | | | |
|---|---|---|---|---|---|---|---|
| Y | Off-white paste | 1686 1466.5 | Heavy products | Tris-trimer | Bis-trimer | Trimer | HDI |
| Nd | Off-white paste | 1689.5 1463.5 | Heavy products | Tris-trimer | Bis-trimer | Trimer | HDI |
| Sm | Yellowish paste | 1689 1463.5 | Heavy products | Tris-trimer | Bis-trimer | Trimer | HDI |

During GPC/FTIR analysis, a large part of the reaction mixture remained insoluble in the dichloromethane. It thus appears that the stage present is not that of the unitary trimerization of the monomer, as is testified by the presence of bis-trimer, of tris-trimer and of heavy compounds with isocyanate functional groups. The quantitative analyses of the entities present cannot therefore be taken into account. An influence of the metal center cannot be demonstrated. However, it may be concluded that all the complexes of rare earth metals and in particular of lanthanide metals make possible trimerization of the HDI monomer.

EXAMPLE 15

Influence of the Amount of Catalyst

The study was carried out on the catalyst Y[N(SiMe$_3$)$_2$]$_3$.

| Catalyst percent by mass | Appearance of the RM | Trimer bands in cm$^{-1}$ | Entities present and their amounts (GPC/FTIR analysis) | | | | DC | |
|---|---|---|---|---|---|---|---|---|
| 1% | Off-white paste | 1686 1466.5 | Heavy products | Tris-trimer | Bis-trimer | Trimer | HDI | |
| 0.2% | Yellowish viscous liquid | 1686.5 1465 | Heavy products 1.2% | Tris-trimer 0.9% | Bis-trimer 2.9% | Trimer + biuret 12.3% | HDI 40.5% | Ov: 31% T + B: 21% |
| 0.1% | Yellowish viscous liquid | 1686 1460 | | | Bis-trimer 0.7% | Trimer + biuret 6.3% | HDI 83.3% | Ov: 8% T + B: 7% |

On reducing the amount of catalyst, the reaction does not go as far.

EXAMPLE 16

Influence of the Temperature

The tests are carried out on reaction mixtures comprising 0.1% by mass of catalyst Y[N(SiMe$_3$)$_2$]$_3$.

| T in ° C. | Appearance of the RM | Trimer bands in cm$^{-1}$ | Entities present and their amounts (GPC/FTIR analysis) | | | | DC |
|---|---|---|---|---|---|---|---|
| 60 | Yellowish viscous liquid | 1686.5 1465 | | | Bis-trimer 0.7% | Trimer + biuret 6.3% | HDI 83.3% | Ov: 8% T + B: 7% |
| 100 | Yellowish viscous liquid | 1689 1464.5 | Heavy products 0.8% | Tris-trimer 0.4% | Bis-trimer 2.1% | Trimer 13% | HDI 64.3% | Ov: 25% T: 20% |

Trimerization from Benzimidinate or "Siam" (Examples 17, 18)

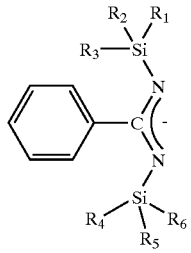

EXAMPLE 17

Comparison Between Samarium and Na

The handling operations were carried out according to the same procedures above.

| Catalyst | Percentage by mass | Appearance of the crude product | Trimer bands observed in cm$^{-1}$ |
|---|---|---|---|
| Sm(Siam)$_3$PhCN | 1% | Opaque paste | 1688.5 1464 |
| NaSiam | 1% | Opaque solid | 1686 1465.5 |
| LiSiam | 1% | Opaque solid | 1689 1465 |

As the 3 reaction mixtures exhibit insoluble materials, the GPC/FTIR analysis was not able to make it possible only to qualify the entities present. It indicates the presence of trimer, of bis-trimer, of tris-trimer and of heavy compounds with isocyanate functional groups predominantly exhibiting at least one isocyanuric ring. The trimerization stage is too advanced to be able to carry out meaningful measurements; catalysis is, however, very strong.

Study of the Influence of the Experimental Parameters

Influence of the Nature of the Metal Center

| Metal center | Appearance of the RM | Trimer bands in cm$^{-1}$ | Entities present (GPC/FTIR analysis) | | | | |
|---|---|---|---|---|---|---|---|
| Sm | Opaque paste | 1688.5 1464 | Heavy products | Tris-trimer | Bis-trimer | Trimer | HDI |
| Yb | Opaque paste | 1688.5 1463 | Heavy products | Tris-trimer | Bis-trimer | Trimer | HDI |
| Y | Off-white paste | 1688.5 1463 | Heavy products | Tris-trimer | Bis-trimer | Trimer | HDI |

The presence of insoluble materials does not make it possible to quantify the crude products obtained. All the rare earth metal salts constitute powerful trimerization catalysts.

EXAMPLE 18

Influence of the Amount of Catalyst (Yttrium Metal)

| Content as % by mass | Appearance of the RM | Trimer bands in cm$^{-1}$ | Entities present and their amounts (GPC/FTIR analysis) | | | | | DC |
|---|---|---|---|---|---|---|---|---|
| 1% | Off-white paste | 1688.5 1463 | Heavy products | Tris-trimer | Bis-trimer | Trimer | HDI | |
| 0.2% | Yellowish viscous liquid | 1686 1460 | Heavy products 2.7% | Tris-trimer 1.7% | Bis-trimer 4.3% | Trimer + biuret 13.4% | HDI 41.3% | Ov: 35% T + B: 21% |

The decrease in the amount of catalyst led to the disappearance of the insoluble materials and made it possible to weaken the trimerization stage.

Cyclotrimerization of the IPDI (Isophorone Diisocyanate) Monomer

EXAMPLE 19

Comparison Between the Yttrium Salt and NaN(SiMe$_3$)$_2$

The tests were carried out under the same operating conditions as for the HDI monomer (cf. EXAMPLE 12).

| Catalyst | Appearance of the RM | Trimer bands in cm$^{-1}$ | Entities present and their amounts (GPC/FTIR analysis) | | | |
|---|---|---|---|---|---|---|
| Y(N(SiMe$_3$)$_2$)$_3$ (1% by mass) | Yellowish liquid | Not very significant | Heavy products | Biuret + trimer | Urea | Carbamate IPDI |
| NaN(SiMe$_3$)$_2$ (1% by mass) | Yellowish paste | 1692 1446.5 | Heavy products | Tris-trimer | Bis-trimer | Trimer IPDI |

As predicted, the yield depends on the associated cation. The efficacy of the alkali metal salt is much higher than that of the yttrium salts.

From the viewpoint of an industrial application, the reaction time and/or the amount of catalyst should be reduced for the alkali metals or the operating conditions should be tightened for the yttrium salts.

Study of the Influence of Experimental Parameters

As the trimerization of the IPDI under the preceding conditions does not give satisfactory results, the operating parameters will thus be modified.

EXAMPLE 20

Influence of the Nature of the Associated Cation
(Same Anion as in Example 19)

| Metal center | Appearance of the RM | Trimer bands in cm$^{-1}$ | Entities present and their amounts (GPC/FTIR analysis) | | | | DC |
|---|---|---|---|---|---|---|---|
| Y | Yellowish, not very viscous, liquid | Weak | Trimer + biuret | Urea | Carbamate | IPDI | |
| Sm | Yellowish, not very viscous, liquid | Weak | Trimer + biuret 1.5 | Urea 4.3% | Dimer 0.4% | IPDI 76% | Ov: 0.1% |

The operating conditions are too mild for these associated cations.

Samarium gives somewhat better results and formation of dimer.

Neodymium gives similar results to those of yttrium.

The lanthanides appear to be less effective than the other rare earth metals (Y, Sc).

EXAMPLE 21

Influence of the Temperature

The study of this parameter was carried out on the yttrium HMDZ salt at 1%.

| T in °C. | Appearance of the RM | Trimer bands in cm$^{-1}$ | Entities present and their amounts (GPC/FTIR analysis) | | | | DC |
|---|---|---|---|---|---|---|---|
| 60 | Yellowish, not very viscous, liquid | Weak | Biuret + trimer | Urea | Carbamate | IPDI | |
| 100 | Yellowish, not very viscous, liquid | Yes | Biuret + trimer 2.2% | Urea 5% | Carbamate | IPDI 53% | Ov: 14% T + B: 4% |

A rise in temperature thus appears to promote the condensation of the IPDI monomer. A test with 5% of catalyst at the same temperature (100° C.) made it possible to increase the condensation and to obtain better degrees of conversion (Ov: 26% and T: 16%).

Trimerization from the Benzimidinate (Siam) Complexes

EXAMPLE 22

Comparison between the Samarium Complex Salt and Na-siam Salt

| Catalyst | Percentage by mass | Appearance of the crude product | Trimer bands observed in cm$^{-1}$ |
|---|---|---|---|
| Sm(Siam)$_3$PhCN | 1% | Yellow, not very viscous, liquid | Not significant |
| NaSiam | 1% | Yellow paste | 1690 1445 |

After washing with pentane, the GPC/FTIR analysis shows the presence of trimer, of bis-trimer, of tris-trimer and of heavy compounds with isocyanate functional groups for the salt. For the samarium salt, the presence of trimer could not be demonstrated; on the other hand, the small amount of biuret and of condensed compounds is found.

EXAMPLE 23

Study of the Influence of the Experimental Parameters

Influence of the Amount of Catalyst (Sm(siam)$_3$PhCN)

| Percentage by mass | Appearance of the RM | Entities present (GPC/FTIR analysis) | | | |
|---|---|---|---|---|---|
| 1% | Yellow, not very viscous, liquid | Biuret | Urea | Carbamate | IPDI |
| 5% | Yellowish, not very viscous, liquid | Biuret + trimer | Urea | Carbamate | IPDI |

The increase in catalyst makes it possible to give a better demonstration of the formation of trimer and of other condensations.

An increase in the temperature makes it possible to obtain higher is yield.

Thus, a test was carried out at 100° C. with an yttrium salt at 5%. The analyses show the presence of trimer and of biuret with the following degrees of conversion: Ov: 16.5% and T+B: 9%.

What is claimed is:

1. A method for the (cyclo)condensation of an isocyanate functional group comprising using a saline compound as a catalyst, said saline compound is selected from the group consisting of substituents having the formula:

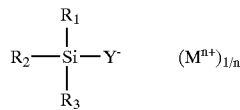

where $(M^{n+})_{1/n}$ represents the cocation(s) necessary for the electrical neutrality of said saline compound balancing the anion of formula (1):

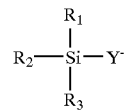

where Y$^-$ is selected from:
a negatively charged oxygen;
and a carbonaceous radical comprising a negative charge carried by an atom from Group VB or by an oxygen, and for which the bond with the silicon of the above formula (I) is carried by an atom from Group VB;
where R$_1$, R$_2$ and R$_3$, which are identical or different, represent a monovalent hydrocarbonaceous group advantageously having from 1 to 30 carbon atoms which is optionally substituted by one or more halogen atoms or CN or ester groups and/or is optionally interrupted by one or more atoms selected from O, N and Si; and
from the salts for which the anionic compound(s) (carrying a negative charge) carry a trialkylsilyl group and result(s) from the reaction of said compounds of formula (I) and of an isocyanate functional group.

2. The method as claimed in claim 1, wherein Y represents a radical of formula (II):

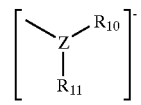

in which:
Z represents a semimetal from Group VB;
R$_{10}$ is a radical having 1 to 30 carbon atoms; and
R$_{11}$ is selected from a negative (anionic) charge and a carbonaceous group attached to Z via a carbon simultaneously of sp$^2$ hybridization and carrying a nitrogen, the nitrogen of which carries a negative (anionic) charge.

3. The method as claimed in claim 1, in which at least one of the R$_1$, R$_2$ and R$_3$ groups is interrupted by several atoms selected from O, N and Si, forming the sequence (I'):

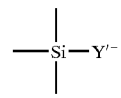

in which Y'$^-$ represents a negatively charged oxygen or a sequence (II'):

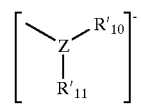

in which
Z' represents a semimetal from Group VB;
R'$_{10}$ represents a hydrocarbonaceous group connected to the Z' radical via a carbon or a silicon (cf. R$_{10}$ radical);
R'$_{11}$ is the negative charge of Y' or a sequence on a nitrogen atom of Y' comprising an sp carbon simultaneously bonded to Z' and carrying a nitrogen carrying the negative charge.

4. The method as claimed in claim 2, wherein, when $R_{11}$ represents a negative charge, $R_{10}$ exhibits at most 30 carbon atoms and is selected from hydrocarbonaceous radicals, and from carbonaceous groups attached to Z via a carbon which simultaneously is of sp$^2$ hybridization and carries a nitrogen.

5. The method as claimed in claim 2, wherein, when $R_{11}$ represents a negative charge, $R_{10}$ exhibits at most 30 carbon atoms and is selected from alkyl or silyl radicals and carbonaceous groups attached to Z via the carbon of sp$^2$ hybridization an iminomethylenyl sequence

or of a —CO—N< sequence.

6. The method as claimed in claim 4, wherein $R_{10}$ is of formula:

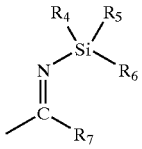

in which:
- $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si;
- $R_7$ represents a hydrocarbonaceous radical of at most 30 carbon atoms.

7. The method as claimed in claim 2, wherein $R_{10}$ is of formula:

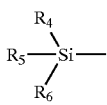

and $R_{11}$ represents a negative charge or is of formula:

in which:
- $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si;
- $R_7$ represents a hydrocarbonaceous radical of at most 30 carbon atoms.

8. The method as claimed in claim 1, wherein the compound of formula (I) corresponds to one of the following formulae (Va) or (Vb):

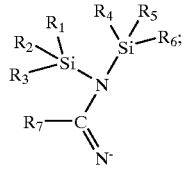
(Va)

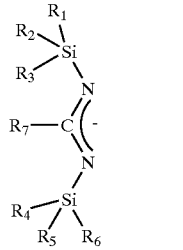
(Vb)

in which:
- $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si;
- $R_7$ represents a hydrocarbonaceous radical of at most 30 carbon atoms.

9. The method as claimed in claim 1, wherein said compound of formula (I) is selected from the compounds of formulae (1) and (2):

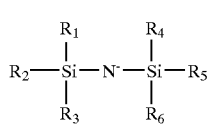
(1)

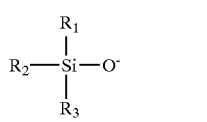
(2)

where $R_1$, $R_2$, $R_3$, $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si.

10. The method as claimed in claim 1, wherein said cocations are selected from oniums and metal cations having only a single stable oxidation state or in their lowest oxidation state (elemental state excepted).

11. The method as claimed in claim 1, wherein said cocations are selected from the group consisting of alkali metal cations and oniums.

12. The method as claimed in claim 1, wherein said cocations are selected from the group consisting of metal cations of transition metals.

13. The method as claimed in claim 1, wherein said cocations are selected from the group consisting of cations of rare earth metals.

14. The method as claimed in claim 12, wherein said cocations are selected from the group consisting of cations of lanthanum and of lanthanide metals.

15. The method as claimed in claim 12, wherein said cocations are cations of erbium.

16. The method as claimed in claim 1, wherein said cocations are the tin(II) cation.

17. A process for the catalytic (cyclo)condensation of isocyanate monomers, comprising:
   a) reaction of the starting isocyanate monomers with a catalyst comprising an inorganic or organic salt of an anionic compound of formula (I):

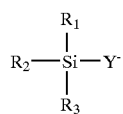

(I)

where Y⁻ is selected from:
   a negatively charged oxygen;
   and a carbonaceous radical comprising a negative charge carried by an atom from Group VB or by an oxygen, and for which the bond with the silicon of the above formula (I) is carried by an atom from Group VB;
   where $R_1$, $R_2$ and $R_3$, which are identical or different, represent a monovalent hydrocarbonaceous group having from 1 to 30 carbon atoms which is optionally substituted by one or more halogen atoms or CN or ester groups and/or is optionally interrupted by one or more atoms selected from O, N and Si;
   b) at a temperature of at least 20° C. and of at most 200° C.,
   c) halting of the (cyclo)condensation reaction at the desired degree of conversion; and
   d) optional removal of the unreacted monomers or the reaction with other compounds which react with the isocyanate functional group.

18. The process as claimed in claim 17 for the catalytic (cyclo)condensation of isocyanate monomers, wherein the anionic compound of formula (I) is selected from the compounds corresponding to one of the formulae below:

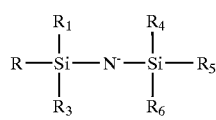

(1)

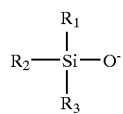

(2)

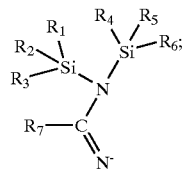

(Va)

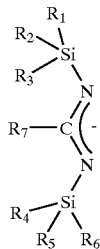

(Vb)

in which:
   $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or ON or ester groups and/or is optionally interrupted by one or more atoms selected from O, S, N and Si;
   $R_7$ represents a hydrocarbonaceous radical of at most 30 carbon atoms.

19. The process as claimed in claim 17 for the catalytic (cyclo)condensation of isocyanate monomers, wherein the anionic compound of formula (I) is selected from the compounds below:

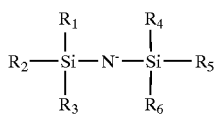

(1)

where $R_1$, $R_2$, $R_3$, $R_4$, $R_5$ and $R_6$, which are identical or different, represent a monovalent aliphatic, cycloaliphatic, which is saturated or unsaturated, aryl, aralkyl or alkylaryl group of hydrocarbonaceous nature having from 1 to 30 carbon atoms which is optionally substituted by one or more halogen atoms or CN or ester groups and/or is optionally interrupted by one or more atoms selected from O, S, N and Si,
   one of $R_1$, $R_2$, $R_3$, $R_4$, $R_5$ and $R_6$ represents a unit of formula:

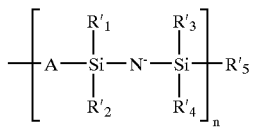

in which A represents an alkylene chain having from 1 to 30 carbon atoms, which is optionally substituted by one or more halogen atoms or CN or ester groups and/or is optionally interrupted by one or more atoms selected from O, S, N and Si, and $R'_1$ to $R'_5$, which are identical or different, representing a monovalent aliphatic,
cycloaliphatic, which is saturated or unsaturated, aryl, aralkyl or alkylaryl group of hydrocarbonaceous nature which is optionally substituted by one or more halogen atoms or CN or ester groups and/or is optionally interrupted by one or more atoms selected from O, S, N and Si, and
n is an integer between 1 and 50, or
   two from $R_1$, $R_2$ and $R_3$, on the one hand, and/or $R_4$, $R_5$ and $R_6$, on the other hand, together constitute a divalent hydrocarbonaceous group which is optionally substituted by one or more halogen atoms or CN or ester groups and/or is optionally interrupted by one or more atoms selected from O, S, N and Si, and/or at least one group selected from $R_1$, $R_2$ and $R_3$ forms, with at least one group from $R_4$, $R_5$ and $R_6$, a divalent hydrocarbonaceous group which is optionally substituted by one or more halogen atoms or CN or ester groups and/or is optionally interrupted by one or more atoms selected from O, S, N and Si, or a precursor of said compound.

20. The process as claimed in claim 19, wherein $R_1$ to $R_6$ and $R'_1$ to $R'_5$, which are identical or different, represent:

an alkyl, alkenyl, haloalkyl or haloalkenyl group having from 1 to 20 carbon atoms which is optionally substituted by chlorine and/or fluorine atoms and/or is optionally interrupted by one or more nitrogen and/or silicon atoms, a cycloalkyl, cycloalkenyl, halocycloalkyl or halocycloalkenyl group having from 3 to 30 carbon atoms and comprising chlorine and/or fluorine atoms and/or which is optionally interrupted by one or more nitrogen and/or silicon atoms, an aryl, alkylaryl or haloaryl group having from 6 to 30 carbon atoms and comprising chlorine and/or fluorine atoms, a cyanoalkyl group having from 1 to 6 carbon atoms, or two groups from $R_1$, $R_2$ and $R_3$ or $R_4$, $R_5$ and $R_6$ together form a divalent radical comprising from 2 to 5 carbon atoms and/or which is optionally interrupted by one or more nitrogen and/or silicon atoms, or two from $R_1$, $R_2$ and $R_3$, on the one hand, and/or $R_4$, $R_5$ and $R_6$, on the other hand, together constitute a divalent hydrocarbonaceous group and/or which is optionally interrupted by one or more nitrogen and/or silicon atoms, or at least one group selected from $R_1$, $R_2$ and $R_3$ forms, with at least one group from $R_4$, $R_5$ and $R_6$, a divalent hydrocarbonaceous group comprising from 2 to 5 carbon atoms and/or which is optionally interrupted by one or more nitrogen and/or silicon atoms.

21. The process as claimed in claim 18, wherein $R_1$ to $R_6$, which are identical or different, are selected from the group consisting of methyl, ethyl, propyl, isopropyl, butyl, isobutyl, α-pentyl, t-butyl, chloromethyl, dichloromethyl, α-chloroethyl, α,β-dichloroethyl, fluoromethyl, difluoromethyl, α,β-difluoroethyl, 3,3,3-trifluoropropyl, trifluorocyclopropyl, 4,4,4-trifluorobutyl, 3,3,3,4,4,5,5-heptafluoropentyl, β-cyanoethyl, γ-cyanopropyl, phenyl, p-chlorophenyl, m-chlorophenyl, 3,5-dichlorophenyl, trichlorophenyl, tetrachlorophenyl, o-, p- or m-tolyl, α,α,α-trifluorotolyl and xylyl groups;

or two groups from $R_1$, $R_2$ and $R_3$ or $R_4$, $R_5$ and $R_6$ represent a dimethylene, trimethylene, tetramethylene or pentamethylene group and/or $R_1$ and $R_4$, taken together, represent a group selected from ethylene, propylene, butylene, pentylene, methylene and trimethylene.

22. The process as claimed in claim 20, wherein $R_1$ to $R_6$ and $R'_1$ to $R'_5$, which are identical or different, are selected from methyl, ethyl, propyl, vinyl and phenyl, these groups optionally being chlorinated and/or fluorinated.

23. The process as claimed in claim 17, wherein the compound of formula (1) is selected from the group consisting of the salts of the following compounds:

hexamethyldisilazane,
1,3-diethyl-1,1,3,3-tetramethyldisilazane,
1,3-divinyl-1,1,3,3-tetramethyldisilazane,
hexaethyldisilazane,
1,3-diphenyl-1,1,3,3-tetramethyldisilazane,
hexamethylcyclotrisilazane, and
2,5-ethylene-2,2,5,5-tetramethylcyclodisilazane.

24. The process as claimed in claim 18, wherein the compound of general formula (2) is selected from the group consisting of:

trimethylsilanolate,
triethylsilanolate,
ethyldimethylsilanolate, and
vinyldimethylsilanolate.

25. The process as claimed in claim 18, wherein the salt of the compound of formula (I) is an erbium salt of the compound of formula (1) and corresponds to the following general formula ($1^E$):

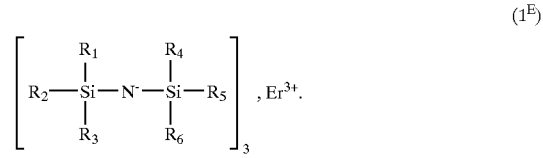

26. The process as claimed in claim 25, wherein the erbium salt is selected from the group consisting of erbium salts of hexamethyldisilazane, 1,3-diethyl-1,1 3,3-tetramethyldisilazane, 1,3-divinyl-1,1,3,3-tetramethyldisilazane, hexaethyldisilazane and 1,3-diphenyl-1,1,3,3-tetramethyldisilazane.

27. The process as claimed in claim 18, wherein the salt of the compound of formula (I) is a tin(II) salt of the compound of formula (1) and corresponds to the following general formula ($1^S$):

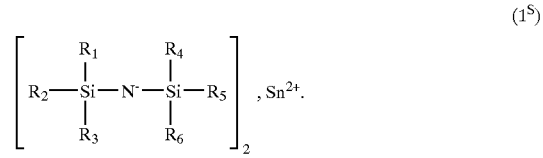

28. The process as claimed in claim 27, wherein the tin(II) salt is selected from the group consisting of tin salts of hexamethyldisilazane, 1,3-diethyl-1,1,3,3-tetramethyldisilazane, 1,3-divinyl-1,1,3,3-tetramethyldisilazane, hexaethyldisilazane, 1,3-diphenyl-1, 1,3,3-tetramethyldisilazane, hexamethylcyclotrisilazane and 2,5-ethylene-2,2,5,5-tetramethylcyclodisilazane.

29. The process as claimed in claim 17, wherein the starting isocyanate is a diisocyanate in which at least one isocyanate functional groups are carried by a carbon atom in the secondary, tertiary or neopentyl cycloaliphatic position.

30. The process as claimed in claim 17, wherein said isocyanate is a cycloaliphatic isocyanate in which at least one isocyanate functional groups is distant from the closest ring by at most one carbon atom.

31. The process as claimed in claim 30, wherein the isocyanate is IPDI.

32. The process as claimed in claim 17, wherein the molar ratio of amount of catalyst to amount of NCO functional groups is at least $5 \times 10^{-5}$ and at most $5 \times 10^{-3}$.

33. An isocyanate composition, comprising compounds carrying isocyanate functional groups, and a saline compound selected from those corresponding to the formula:

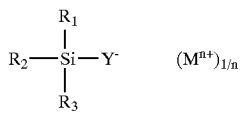

where $(M^{n+})_{1/n}$ is the cocation(s) necessary for the electrical neutrality of said saline compound balancing the anion of formula (I):

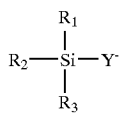 (I)

where $Y^-$ is selected from:
  a negatively charged oxygen;
  or a carbonaceous radical comprising a negative charge carried by an atom from Group VB or by an oxygen, and for which the bond with the silicon of the above formula (I) is carried by an atom from Group VB;
  where $R_1$, $R_2$ and $R_3$, which are identical or different, represent a monovalent hydrocarbonaceous group advantageously having from 1 to 30 carbon atoms which is optionally substituted by one or more halogen atoms or CN or ester groups and/or is optionally interrupted by one or more atoms selected from O, N and Si; and
  from the salts for which the anionic compound(s) carry a trialkylsilyl group and result(s) from the reaction of said compounds of formula (I) and of an isocyanate functional group, the molar ratio of amount of catalyst to amount of NCO functional groups is at least $5 \times 10^{-5}$ and at most $5 \times 10^{-2}$.

34. The isocyanate composition as claimed in claim 33, wherein the concentration of isocyanate functional groups is between 0.5 and 7 equivalents per liter.

35. The isocyanate composition as claimed in claim 33, which comprises, by mass, at least 1% of a compound exhibiting at least one unit:

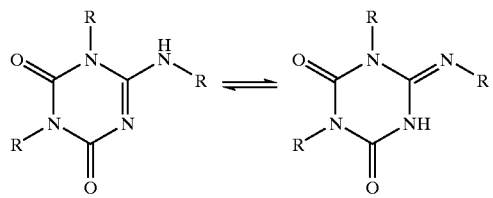

where the R groups, which are identical or different, represent the residues of the monomer or monomers after discounting one of the isocyanate functional groups, it being possible for the others to be involved in a separate condensation.

36. The isocyanate composition as claimed in claim 33, which comprises, by mass, at least 1% of a compound exhibiting at least one unit:

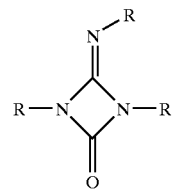

where the R groups, which are identical or different, represent the residues of the monomer or monomers after discounting one of the isocyanate functional groups, it being possible for the others to be involved in a separate condensation.

37. The isocyanate composition as claimed in claim 33, which has been employed with erbium salts and wherein it comprises from 50 to 80% by weight of trimeric compounds composed of monoisocyanates and 6-amino-5-azauracils, from 0.5 to 5% of monouretidinedione compounds and less than 1% by weight of isocyanate monomers, with respect to the total weight of the isocyanate compounds present in the composition.

38. The isocyanate composition as claimed in claim 33, which has been employed with tin salts and comprises from 50 to 75% by weight of mono-2-imino-4-oxo-1,3-diazetidine compounds, from 10 to 25% by weight of bis(2-imino-4-oxo-1,3-diazetidine) compounds, from 10 to 25% by weight of isocyanate-ureas and less than 1% by weight of isocyanate monomers, with respect to the total weight of the isocyanate compounds present in the composition.

39. The isocyanate composition as claimed in claim 33, which comprises less than 1% by weight of isocyanate monomers with respect to the total weight of the isocyanate compounds present in the composition, said composition comprising from 0.5 to 100% of isocyanate functional groups masked using an agent which masks the isocyanate functional group.

40. A method for the preparation of coating products, paints and varnishes, of adhesives, of inks, of biocides or of detergents comprising using an isocyanate composition as claimed in claim 33.

* * * * *

UNITED STATES PATENT AND TRADEMARK OFFICE
CERTIFICATE OF CORRECTION

PATENT NO.   : 6,946,538 B2
DATED        : September 20, 2005
INVENTOR(S)  : Jean-Marie Bernard et al.

It is certified that error appears in the above-identified patent and that said Letters Patent is hereby corrected as shown below:

<u>Title page,</u>
Item [75], Inventors, change "Visseau" to -- Visseaux --.

Signed and Sealed this

Twenty-seventh Day of December, 2005

JON W. DUDAS
*Director of the United States Patent and Trademark Office*